United States Patent [19]
Nakamura et al.

[11] Patent Number: 5,912,113
[45] Date of Patent: Jun. 15, 1999

[54] METHOD AND APPARATUS FOR CONTROLLING CARBON SOURCE CONCENTRATION IN AEROBIC CULTIVATION OF A MICROORGANISM

[75] Inventors: Takashi Nakamura; Tatsuya Nakayama, both of Kawasaki; Yosuke Koyama; Keishi Shimazaki, both of Saga-gun; Harufumi Miwa, Kawasaki; Minoru Tsuruta, Kawasaki; Koji Tamura, Kawasaki; Osamu Tosaka, Saga-gun, all of Japan

[73] Assignee: Ajinomoto Co., Inc., Tokyo, Japan

[21] Appl. No.: 08/905,713

[22] Filed: Aug. 4, 1997

Related U.S. Application Data

[63] Continuation of application No. 08/535,324, Sep. 27, 1995, abandoned, which is a continuation of application No. 08/280,256, Jul. 25, 1994, abandoned, which is a continuation of application No. 08/137,960, Oct. 19, 1993, abandoned, which is a continuation of application No. 07/797,061, Nov. 25, 1991, abandoned.

[30] Foreign Application Priority Data

Nov. 30, 1990 [JP] Japan .................................. 2-339687
Mar. 12, 1991 [JP] Japan .................................. 3-126992
Oct. 24, 1991 [JP] Japan .................................. 3-277938

[51] Int. Cl.$^6$ .............................. C12Q 3/00; C12N 1/12; C12N 1/20; C12N 1/14
[52] U.S. Cl. ...................... 435/3; 435/252.1; 435/254.2; 435/255.1; 435/256.8; 435/289.1; 435/822; 435/948
[58] Field of Search .............. 435/3, 252.1, 254.2, 435/255.1, 256.8, 289.1, 822, 968

[56] References Cited

U.S. PATENT DOCUMENTS

| | | | |
|---|---|---|---|
| 3,002,894 | 10/1961 | Rungaldier et al. | 435/3 |
| 3,010,881 | 11/1961 | Markhof | 435/3 |
| 3,857,757 | 12/1974 | Herrick et al. | 435/289 |
| 3,926,738 | 12/1975 | Wilson et al. | 435/289 |
| 3,929,582 | 12/1975 | Kellner | 435/289 |
| 3,941,662 | 3/1976 | Munder et al. | 435/289 |
| 4,073,692 | 2/1978 | Ciaccio et al. | 435/289 |
| 4,411,991 | 10/1983 | Hirakawa et al. | 435/42 |
| 4,680,267 | 7/1987 | Eppstein et al. | 435/289 |
| 5,316,905 | 5/1994 | Mori et al. | 435/3 |
| 5,318,909 | 6/1994 | De Baere | 435/291 |

FOREIGN PATENT DOCUMENTS

| | | | |
|---|---|---|---|
| 2092686 | 1/1972 | France | 435/289 |
| 26 57 209 | 6/1978 | Germany . | |
| 2657209 | 6/1978 | Germany | 435/289 |
| 0220852 | 4/1985 | Germany | 435/289 |
| 1127901 | 12/1984 | Russian Federation | 435/289 |
| 1332192 | 10/1973 | United Kingdom . | |

OTHER PUBLICATIONS

English translation of German Patent # 0,220,852, Apr. 1985.
English translation of German Patent #2,657,209, Jun. 1978.

*Primary Examiner*—Lynette F. Smith
*Assistant Examiner*—Brett Nelson
*Attorney, Agent, or Firm*—Oblon, Spivak, McClelland, Maier & Neustadt, P.C.

[57] ABSTRACT

The present invention is a method for aerobically cultivating yeast or bacteria in a culture medium of fed-batch, continuous or cell-recycling continuous cultures, wherein the carbon source concentration in the culture medium is maintained at a constant low level of under g/l. The carbon source concentration is maintained by measuring the carbon consumption of a culture of the yeast or bacteria in a preliminary experiment. The rate is determined between the time the culture is started and a time when the carbon source is exhausted. A feeding time is then determined wherein the activity of the yeast or bacteria in the presence of the carbon source does not change and a volume of the carbon source to be used in a first feeding (So) is set as $So = v \times T$. Then, in a main culture, a first feeding of a volume of the carbon source (So) is added for the time (T), and the exhaustion of the carbon source is detected as an increase in pH or an increase in concentration of oxygen dissolved in the culture medium. A second feeding of a volume of the carbon source is then added for the time (T), and the feeding rate is determined based on a period ($\tau$) before which the second feeding is added as follows:

if 10 min. $\geq \tau$, the feeding rate of the feed solution is set at $1.1 \times v$;

if 30 min. $\geq \tau > 10$ min., the feeding rate of the feed solution is set at $v$;

if 60 min. $\geq \tau > 30$ min., the feeding rate is set at $0.9 \times v$; or if 120 min. $\geq \tau > 60$ min., the feeding rate is set at $0.8 \times v$. By modifying the feeding rate in this way, the carbon source concentration in the cultivation vessel is kept at the constant low level of under 5 g/l.

3 Claims, 6 Drawing Sheets

METHOD AND APPARATUS FOR CONTROLLING CARBON SOURCE CONCENTRATION IN AEROBIC CULTIVATION OF A MICROORGANISM

This application is a Continuation of application Ser. No. 08/535,324, filed on Sep. 27, 1995, now abandoned, which is a continuation of Ser. No. 08/280,256, filed on Jul. 25, 1994, now abandoned, which is a continuation of Ser. No. 08/137,960, filed on Oct. 19, 1993, now abandoned, which is a continuation of Ser. No. 07/797,061, filed Nov. 25, 1991, now abandoned.

BACKGROUND OF THE INVENTION

1. Field of the Invention

The present invention relates to a method for controlling the carbon source concentration in aerobic cultivation of a microorganism. In particular, the present invention relates to a method for controlling the substrate carbon source that remains at a low level in a cultivation vessel during the culture feeding in aerobic fed-batch, continuous or cell-recycling continuous cultures. This is accomplished by monitoring the increase in pH or dissolved oxygen content in the culture media and adding the feed solution intermittently into the cultivation vessels at a calculated feed rate using a feed control device controlled by computer. Apparatus suited for practicing such a method is also provided.

The present invention further relates to a process for producing L-lysine by fermentation, which is an important amino acid used as a feed additive for broilers or pigs since L-lysine is in short supply in cereals for feed.

2. Background Information

For purposes of producing various substances by fermentation, for example, various amino acids or nucleic acids, using microorganisms or production of microbial cells for example, yeast cells, microorganisms are aerobically cultured. Aerobic cultivation of a microorganism is industrially performed by fed-batch culture, continuous culture or cell-recycling continuous culture, using carbon source(s) such as sugar, for example, as the main raw material.

In such a cultivation method, it is necessary to keep the concentration of carbon source (substrates) such as sugars in a cultivation vessel at a level as low as possible during the feeding of the culture. In this way several purposes are accomplished such as preventing substrate inhibition by the raw carbon source, reducing the loss of the raw carbon source by effectively utilizing the raw materials for the cultivation, easily isolating the product from the final fermentation broth, and preventing environmental pollution of the remaining carbon source contained in the waste liquid that remains after the product is isolated.

In the case of continuous culturing and cell-recycling continuous culturing, the product is isolated from the culture broth that is continuously discharged even during the feeding of cultures. It is necessary to control the flow amount of the carbon sources, for example, sugars, in the isolation process to the lowest level possible to make the influence of the carbon sources on the isolation process substantially zero. It is also necessary to prevent loss of the raw materials. In this type of cultivation, it has also been desirable to remove the manual operations for analyzing the carbon source concentration by substituting automatic monitoring that controls the stability of the carbon source concentration.

For maintaining the concentration of the carbon source, for example, sugar, at low levels during the feeding of the cultures, previously methods have been described which comprise controlling the carbon source concentration using an independent index such as the amount of oxygen consumed, amount of carbon dioxide gas discharged, pH, amount of the by-product produced, or amount of ammonia added, while adding carbon sources such as sugar in an amount obtained by multiplying them with a predetermined proportional coefficient. According to these methods, the microbial activity during the cultivation cannot be measured with high accuracy so that in some instances the concentration cannot be controlled satisfactorily when the activity has abnormally changed. For these reasons, it is impossible to effectively control the carbon source concentration at a low level (e.g., below 3 g/l) during the cultivation.

Furthermore, there is another known method which discloses detecting the exhaustion of carbon source concentrations in a cultivation vessel during cultivation only by the concentration of dissolved oxygen. However, sensing reliability is poor. Where the state of aeration or agitation (r.p.m. of agitation, an amount of air flow) changes, the concentration of dissolved oxygen greatly changes. In this case, the sensor sometimes incorrectly detects the exhaustion of carbon sources, whereby the carbon source concentration in the cultivation vessel cannot be effectively controlled. For these reasons, this method is not practical either.

Thus, it is clear that a need exists for a method and apparatus that automatically controls the carbon source concentration in the aerobic culturing of microorganisms. The present invention provides such a method and apparatus to overcome the aforementioned problems.

Another aspect of the present invention relates to a process for producing L-lysine by fermentation. Previously, methods have been described comprising the culturing of microorganisms capable of producing L-lysine by a batch or continuous process, accumulating L-lysine in the medium, and collecting the product, L-lysine.

In the case of batch processing, liquid medium containing carbon sources and nitrogen sources are put in a fermenter to perform incubation batchwise. Alternatively, medium containing the carbon source(s) alone are added continuously or intermittently to perform feeding of cultures.

In the case of continuous processing, incubation is carried out by supplying medium to a fermenter continuously and withdrawing the same volume of culture broth continuously to maintain the cell amount or concentration of the product, for example, at a constant level.

Where fermentation of L-lysine is performed by the conventional batch process, the accumulation of the product in the culture broth or the yields are high but there is difficulty in obtaining high productivity. On the other hand, when the conventional continuous process is used, the productivity is high but it is difficult to achieve high accumulation of product or high yields. In order to respond to an increased demand for L-lysine and prepare it at lower costs, it is necessary to enhance the productivity of L-lysine by fermentation and improve the concentration and yield of the product accumulated.

Thus, the need exists to provide a process for producing L-lysine by a fermentation method that alleviates the prior art's technical problems. The present invention combines the advantages of conventional batch processing and continuous processing by providing a novel fermentation method for producing L-lysine with high productivity, high concentration of accumulated product and high yield.

SUMMARY OF THE INVENTION

It is an object of the present invention to provide a method for controlling the carbon source concentration in the aerobic cultivation of a microorganism and an apparatus for use in the practice of such a method. It is a further object of the present invention to provide an improved process for the production of L-lysine by fermentation.

In one embodiment, the present invention relates to a method for aerobic cultivation of a microorganism in fed-batch, continuous or cell-recycling continuous cultures comprising the intermittent addition of a carbon source feed solution to a cultivation vessel that is automatically controlled by a computer.

In another embodiment, the present invention relates to an apparatus for the aerobic cultivation of a microorganism in fed-batch, continuous, or cell recycling continuous cultures comprising a cultivation vessel equipped with sensors for detecting the pH and the concentration of dissolved oxygen of a culture medium in the cultivation vessel, respectively, and with an apparatus for aeration and agitation, of the culture medium, which is designed to receive a feed solution, and control means for controlling a feeding rate of the feed solution into the cultivation vessel, the control means comprising first signal converter for receiving respective signals output by the pH sensor and the dissolved oxygen concentration sensor, and outputting converted signals; computing means for receiving the converted signals, calculating the feed rate using the converted signals, and outputting a feed rate signal; a second signal converter for receiving the feed rate signal and outputting a converted feed rate signal; and a feed rate control means for controlling the feed rate of the feed solution to the cultivation vessel using the converted feed rate signal.

In a further embodiment, the present invention relates to a process for producing L-lysine by fermentation which comprises inoculating a microorganism capable of producing L-lysine in liquid medium, culturing the microorganism while feeding additional medium containing both carbon sources and nutrients having an effect of growth acceleration after the logarithmic growth phase of the microorganism so as to maintain the carbon sources at a concentration of not greater than 5 g/l in the culture medium, and collecting L-lysine produced and accumulated in the medium.

Various other objects and advantages of the present invention will become apparent from the drawings and the following detailed description of the invention.

DETAILED DESCRIPTION OF THE INVENTION

Figure 1:
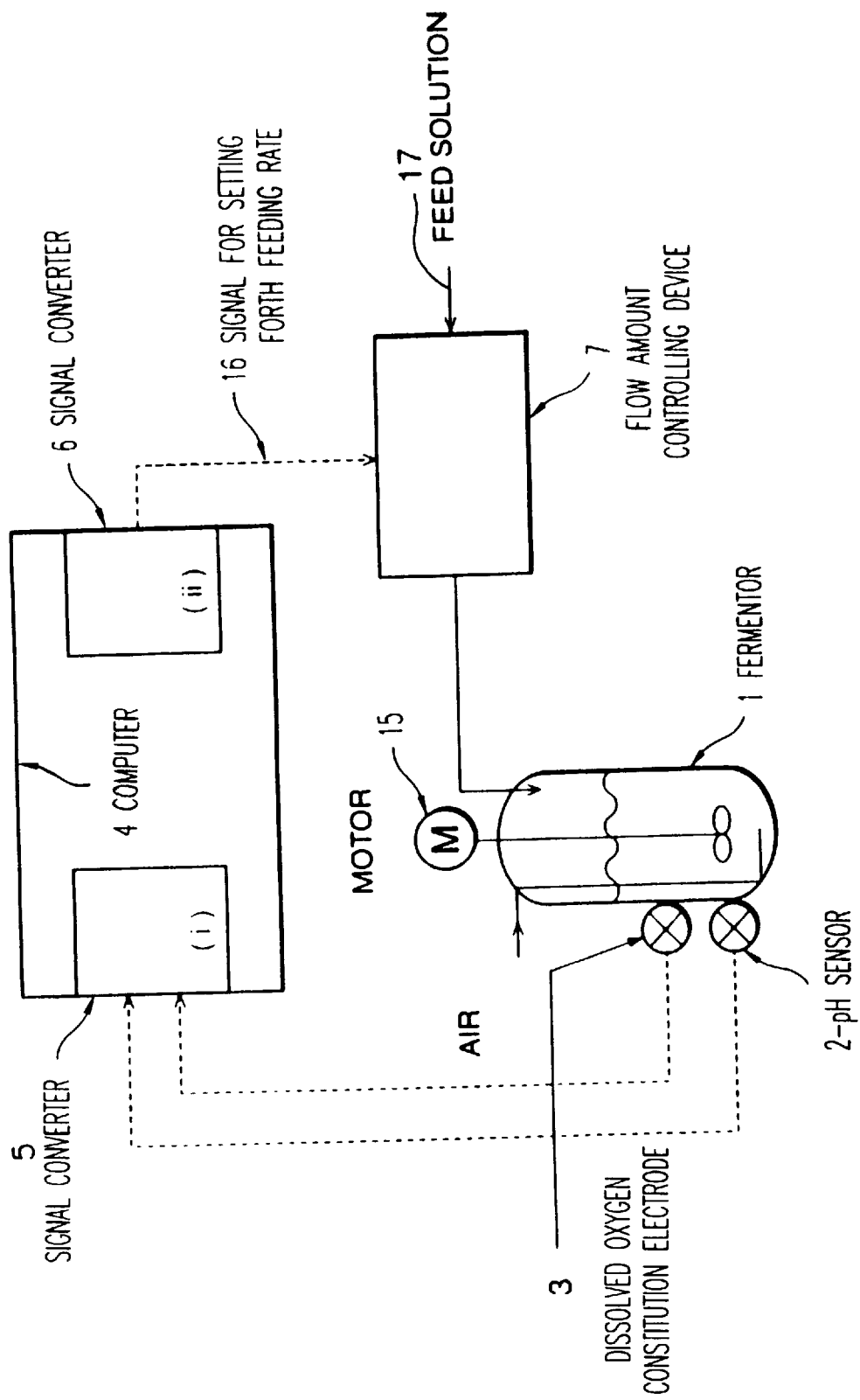
FIG. 1 illustrates an embodiment of the apparatus of the present invention.

The present invention relates, in part, to a method for aerobically culturing a microorganism using fed-bath, continuous, or cell-recycling continuous cultures which has the advantages that the rate of assimilating carbon sources such as sugar by the microorganism during the feeding process can be controlled at an appropriate feeding rate of feed solution of the carbon sources, the exhaustion of the carbon sources can be detected with good reliability and certainty, and the exhaustion of the carbon sources can be detected without being affected by the state of aeration or agitation. Other advantages are also provided in this method.

The present invention also provides an apparatus for practicing the above method.

As a result of extensive investigations to solve the foregoing problems discussed in the Background section, applicants have found that when carbon sources such as sugar are intermittently added to a cultivation vessel in aerobic cultivation by fed-batch culture, continuous culture or cell recycling continuous culture, the feeding rate of the carbon source feed solution at the time of the addition and addition (s) subsequent thereto may be determined using as an index the increase in pH or the increase of dissolved oxygen concentration caused by exhaustion of the carbon sources in the culture medium contained in the cultivation vessel. The feeding rate is monitored and controlled by a computer as the period between the termination of the first addition and subsequent period of feed addition based on increase pH or dissolved oxygen in the cultures, thereby solving the problems in the prior art.

Thus, the present invention relates, in part, to a method for aerobic cultivation of a microorganism in which the first addition of a carbon source feed solution in aerobic fed-batch culture, continuous culture or cell-recycling continuous culture of a microorganism occurs through intermittent addition of the feed solution into the cultivation vessel and is effected by adding the feed solution for a definite period of time at a feeding rate previously determined.

The second addition or subsequent addition(s) is initiated when a computer detects an increase in pH or an increase in concentration of dissolved oxygen caused when the carbon source (substrate) in the cultivation vessel is exhausted at the period of terminating the addition preceding a certain period for the next addition, and is effected by adding the feed solution to the cultivation vessel for a definite period of time. The feeding rate is computed with the computer from the time for the period for terminating the addition and the feeding rate of the feed solution in the period for addition preceding the period for terminating the addition in such a way that the rate becomes smaller when the time for the period of terminating the addition is long and the rate becomes larger when the time for the period of terminating the addition is short.

The method is characterized by automatically controlling the substrate concentration at a constant low level in a cultivation vessel in the aerobic cultivation of the microorganism.

It is well known to subject a microorganism to aerobic fed-batch culture, continuous culture or cell-recycling continuous culture while continuously (herein the term "continuously" is used in a broad sense and also includes "intermittently") feeding a feed solution containing substrate carbon sources, such as sugar, in a cultivation vessel for purposes of producing various substances by fermentation or producing the cells themselves. The aerobic fed-batch culture, continuous culture or cell-recycling continuous culture in the present invention may also be performed by modifying well known methods for fed-batch culture, continuous culture or cell-recycling continuous culture except for the feeding method of the feed solution during the feeding culture herein described.

The first addition of the feed solution during the feeding culture generally starts when the concentration of substrate carbon source(s) such as sugar in the culture medium reaches a certain low level in a main culture preceding the feed culture. The predetermined feeding rate of the feed solution is determined by a preliminary experiment and generally equals the rate of the substrate consumed in the main culture at the time of starting the feeding culture, namely, at the time when the first feeding starts. The definite period of time in the addition of the feed solution is an optional period of time selected within such a range that the activity of a microorganism for consuming the carbon source, such as sugar, does not change greatly (generally in the range of 10 minutes to 24 hours).

When the substrate in the culture medium after completion of the first addition is exhausted, both the pH of the medium and concentration of dissolved oxygen increases. When the increase is detected by the computer via the pH sensor and the dissolved oxygen concentration sensor, the computer instructs the device for controlling the flow rate of feed solution to the cultivation vessel whereby the second addition of the feed solution is initiated.

The increase in pH and the increase in the dissolved oxygen concentration do not necessarily occur concurrently. Where there is a time lag between these two increases, the second addition is initiated, based on the earlier increase detection. The pH sensor and the dissolved oxygen concentration sensor sometimes break down and are calibrated frequently. Therefore, these sensors are not used alone. By using both sensors simultaneously, reliability of detecting the exhaustion of substrate can be markedly improved.

The feeding rate in the second addition of the feed solution is a rate obtained by computing in such a manner that if the period for terminating the addition is long, the rate becomes smaller and if the period is short, the rate becomes larger. This allows a balancing of the rate of the substrate feeding with the rate of consumption of the substrate, thereby maintaining the substrate concentration in the culture medium in the cultivation vessel at a desired low level, based on the period of terminating the addition between the first addition and the second addition, and the feeding rate of the first addition. The computation is made by the computer but such a program for the computer can be easily prepared by one skilled in the art. An example of the program is shown in Example 1 described herein.

The definite time period during which the second addition is performed is determined in a manner similar to the definite time for the first addition. It may not be necessary that the period for the second addition be the same as the period for the first addition, so long as the time period is chosen within such a range that the activity of a microorganism for consuming the carbon source (substrate) such as sugar, for example, does not change greatly. The period of time for each feeding is chosen from the time period in which the activity of a microorganism for consuming the substrate does not change greatly and the substrate concentration in the cultivation vessel can be maintained at a low level during cultivation.

The starting time, feeding rate and period for feeding of the third and subsequent additions of the feed solution are determined similar to the second addition.

Thus, the second and subsequent additions start when the computer detects the increase in pH or the increase in dissolved oxygen concentration caused when the carbon source (substrate) in the cultivation vessel is exhausted during the period of terminating the addition preceding a certain period for addition and are effected for a certain period of time at the feeding rate computed by the computer in such a manner that if the period for terminating the addition is long, the rate becomes smaller and if the period is short, the rate becomes longer, based on the period of terminating the addition and the feeding rate of the preceding addition.

As described above, it is possible to set forth the feeding rate of the feed solution of the substrate carbon source(s) such as sugar, for example, and other conditions for addition, while monitoring the activity of a microorganism point by point. It is also possible to easily control the substrate concentration in the cultivation vessel to the level as low as below 5 g/l, further below 3 g/l.

The present invention also relates to an apparatus used for the method described above comprising: (i) a cultivation vessel equipped with sensors for detecting the pH and the concentration of dissolved oxygen of a culture medium in the cultivation vessel and with an apparatus for aeration and agitation, which is designed to receive a feed solution via a flow rate controlling device, and (ii) a computer equipped with two signal converters wherein (a) the pH sensor and the dissolved oxygen concentration sensor are connected in order that detected data of pH and concentration of dissolved oxygen by the sensors are put into the computer via one signal converter and (b) the flow rate controlling device is connected in order that the feeding rate of the feed solution computed by the computer is transferred to the device via the other signal converter.

The apparatus of the present invention is an apparatus which has the functions to detect the exhaustion of the substrate carbon sources such as sugar, for example, and compute the feeding rate of the carbon source fed solution in the computer, based on the signals transferred to the computer from the pH sensor such as pH electrode, for example, and the dissolved oxygen concentration sensor such as dissolved oxygen electrode, for example, mounted to the cultivation vessel, and transfer the computed feeding rate to the device for controlling the flow rate of the feed solution mounted to the line for feeding carbon sources of the cultivation vessel.

As is well known in the art, pH sensors and dissolved oxygen sensors tend to be broken very often and should be calibrated frequently. According to the present invention, the respective sensors are not used alone but instead are used in combination, whereby reliability of detecting exhaustion of carbon sources such as sugar, for example, can be markedly improved. When each sensor is used alone, the effects are exhibited though the reliability decreases.

In a further embodiment, the present invention relates to a method of fermentation for the production of L-lysine using L-lysine producing bacteria. The present invention provides a method for producing L-lysine that combines the advantages of both conventional continuous fermentation and conventional batch fermentation, those being high productivity, high concentrations of accumulated product and high yields of L-lysine. Applicants have found that by inoculating a microorganism capable of producing L-lysine in liquid medium, culturing the microorganism while feeding feed medium containing both carbon sources and nutrients having an effect of growth acceleration after the logarithmic growth phase of the microorganism so as to maintain the carbon sources at a concentration of not greater than 5 g/l in the culture broth, and collecting L-lysine produced and accumulated in the culture broth, the aforementioned improvements for producing L-lysine are accomplished.

Thus, the present invention related to a process for producing L-lysine by fermentation which comprises inoculating a microorganism capable of producing L-lysine in liquid medium, culturing the microorganism while feeding feed medium containing both carbon sources and nutrients having an effect of growth acceleration after the logarithmic growth phase of the microorganism while maintaining the carbon source at a concentration of not greater than 5 g/l in the culture broth, and collecting L-lysine produced and accumulated in the broth.

In the process of the present invention, there is no particular limitation of the microorganisms capable of producing L-lysine in the present invention as long as the microorganisms are capable of producing L-lysine. Examples of such microorganisms include microorganisms belonging to the genus Brevibacterium or Corynebacterium which possess properties necessary for imparting L-lysine productivity thereto (homoserine auxotrophy, resistance to S-(2-aminoethyl)-L-cysteine, resistance to α-chlorocaprolactam, etc.). More specifically, examples of the microorganisms include *Brevibacterium lactofermentum* ATCC 21800, *Brevibacterium flavum* ATCC 21475 and *Corynebacterium acetoglutamicum* ATCC 21491.

There is no particular limitation to the liquid medium either. Complete liquid medium conventionally known containing organic and inorganic nutrient sources such as a carbon source, nitrogen source and other trace nutrients may be used.

As to the carbon sources used in feeding according to the process of the present invention, any of sugars, organic acids, alcohols and others generally used as raw materials (carbon sources) for fermentation may be used so long as the aforesaid lysine-producing bacteria may assimilate the carbon sources.

The nutrient having an effect of growth acceleration refers to an amino acid, vitamin and a natural matter containing the same which are effective in accelerating the growth of the L-lysine-producing bacteria. Specific examples include soybean protein hydrolysate, yeast extract and corn steep liquor.

As known in the art, the medium feed generally contains carbon sources alone in feed culture and complete in the liquid medium in the continuous process. In the process of the present invention, the medium feed contains both carbon sources and nutrients having the effect of growth acceleration. The use of such feed medium is one of the characteristics of the process of the present invention.

In the process of the present invention, the medium is fed when or after the logarithmic growth of the microorganism is completed. Feeding prior to completion of the logarithmic growth should be avoided since the initial growth of bacteria might be inhibited.

For feeding the medium during or after the logarithmic growth is completed, the feeding may be carried out either continuously or intermittently. Further, where it is expected that the volume of medium in a fermenter would exceed the allowable volume charged in the fermenter, a part of the culture broth is withdrawn out of the fermenter previously, or at the time when the volume reaches the allowance volume, whereby the feeding may further be continued.

Therefore, to be important for the feeding of medium, the medium should be fed so as to maintain the concentration of the carbon sources in the culture broth always at the level of not greater than 5 g/l. This is also one of the characteristic features of the present invention. To maintain the carbon source concentration at the constant level, the culture broth may be subjected to sampling on occasion to directly analyze the concentration of the carbon source. Alternatively, the pH or the concentration of dissolved oxygen may be measured and by sensing a shortage of the carbon source from its change, feeding of the medium may be controlled. Unless the concentration of carbon source is maintained constantly at the level of 5 g/l or less, the growth of bacteria or the rate of forming L-lysine decreases and such a case does not fit the object of the present invention.

The characteristics of the present invention are as described above and there is no particular restrictions on other conditions, for example, fermentation. For example, the temperature for producing L-lysine by fermentation according to the present invention may be any temperature at which the lysine-producing bacteria used can grow and is generally in the range of 25 to 45° C., preferably 30 to 40° C. The pH set forth for the fermentation is generally in the range of 5.8 to 8.5, preferably 6.5 to 7.5. For adjustment of the pH, inorganic or organic acidic or alkaline substances and furthermore, urea, calcium carbonate, or ammonia gas, as examples, may be used.

As the fermenter used in the present invention, any shape may be used as long as the fermenter is conventionally used for amino acid fermentation. For example, one may use a complete mixing tank equipped with a turbine impeller or a fermenter of air lift type.

After completion of the incubation, L-lysine may be collected from the fermentation broth in a conventional manner such as ion exchange resin method, crystallization, and other methods or by a combination thereof.

The following examples are given to further illustrate the present invention without being deemed limitative thereof.

EXAMPLES

Figure 2:
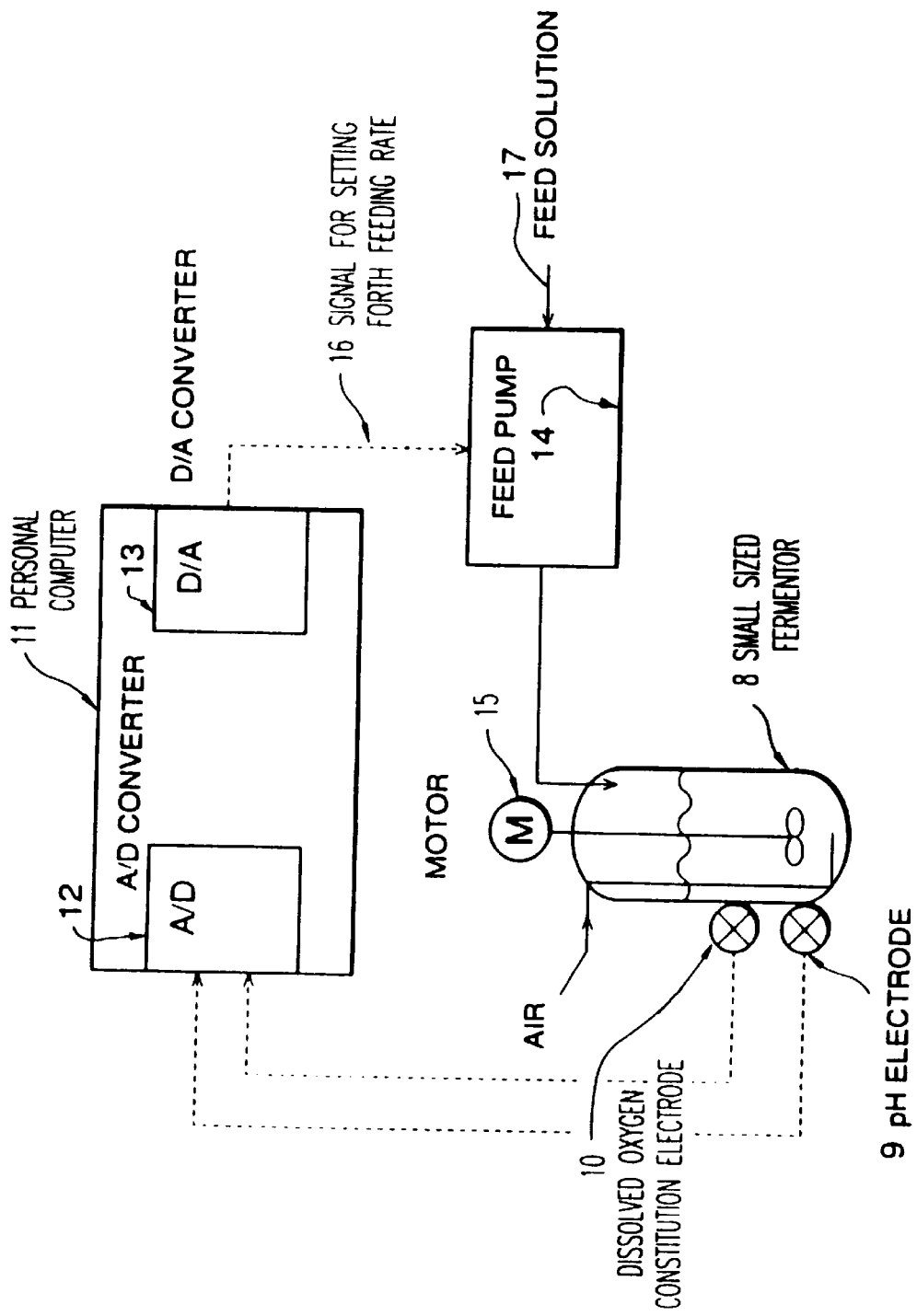
FIG. 2 illustrates the apparatus used in Example 1.
Figure 3:
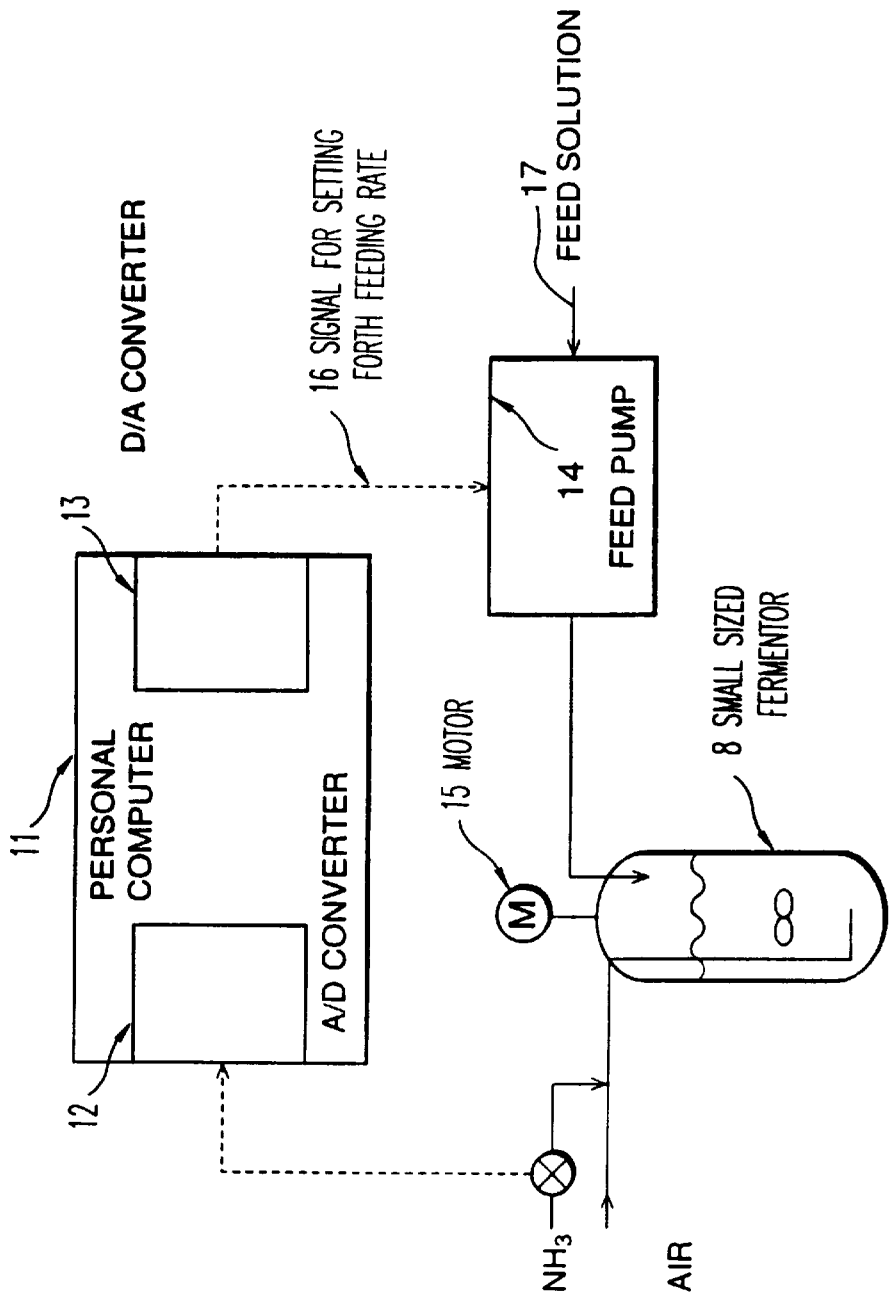
FIG. 3 shows the apparatus used in Comparative Example 1.

In Examples 1–5, the apparatus used is shown in FIG. 2 wherein [8] a small-sized glass-made jar fermenter, [9] pH electrode, [10] dissolved oxygen electrode, [11] a personal computer, [12] an A/D converter, [13] a D/A converter and a [14] feed pump correspond to in the apparatus shown in FIG. 1 to [1] the cultivation vessel (fermenter), [2] the pH sensor, [3] the dissolved oxygen concentration sensor, [4] the computer, [5] signal converter (i) in this computer, [6] signal converter (ii) in this computer and the [7] flow amount controlling device, respectively. In FIGS. 1–3 [15] corresponds to an aeration and agitation device to aerate and agitate the culture medium, including a motor, M. [16] corresponds to the signal for setting forth the feeding rate. [17] corresponds to the feed solution that flows into [14] feed pump or [7] flow amount controlling device.

Example 1
Production of L-glutamic acid by fermentation in cell-recycling continuous culture An aqueous medium (30 ml) containing 30 g/l of glucose, 1 g/l of $KH_2PO_4$, 0.4 g/l of $MgSO_4.7H_2O$, 4 g/l of urea, 20 mg/l of $FeSO_4.7H_2O$, 20 mg/l of $MnSO_4.4H_2O$, 5 ml/l of soybean protein acid hydrolysate and 300 μg/l of biotin was charged in a shake flask of 500 ml volume followed by sterilization for 10 minutes by heating at 115° C. After cooling to room temperature, *Brevibacterium lactofermentum* ATCC 13869 was inoculated on the medium followed by culturing 30° C. for 24 hours.

After the seed culture medium and 270 ml of an aqueous main culture medium containing 80 g/l of cane molasses as sugar, 1 g/l of $KH_2PO_4$ and 10 ml/l of soybean protein acid hydrolysate was charged in a small-sized glass-made jar fermenter of 1 liter volume which had been previously sterilized, the mixture was kept at 30° C. Filter-sterilized air was bubbled at a rate of 300 ml/min and stirring was initiated, while keeping the pH at 7.5 with $NH_3$ gas (initiation of the main culture).

The small-sized glass-made jar fermenter was connected with a 16 bit personal computer as shown in FIG. 2. The analog signals for the pH and the dissolved oxygen concentration detected by the pH electrode and dissolved oxygen concentration electrode, which had been inserted in the jar fermenter, were taken up in the personal computer via the A/D converter built in the personal computer. The feeding rate of the aqueous feed medium (feed solution) which was set forth and computed by the personal computer was transferred to a feed pump as analog signals via the D/A converter built in the personal computer.

At the same time when the main culture began, the following conditions were set on the personal computer: feeding rate of the feed solution added initially (first addition), 30 ml/h; data detected for the exhaustion of the sugar substrate by an increase in pH 7.7; data detected for the exhaustion of sugar substrate by an increase in dissolved oxygen concentration, 20% (ordinary level of the dissolved oxygen concentration is 1 to 10%), and feeding time of the feed solution, 3 hours.

For purpose of inhibiting the growth of the bacteria thereby to produce glutamic acid, polyoxyethylene sorbitan monopalmitate was added in a concentration of 0.2 wt. %, 5 hours after the initiation of the main culture. After the main culture was continued for further 5 hours, the personal computer was put under controllable conditions (automatic running state) and the first addition of the feed solution was initiated at the predetermined feeding rate of 30 ml/h. The feed solution added to the jar fermenter contained 180 g/l of cane molasses as sugar, 5 ml/l of soybean protein acid hydrolysate and 0.2 wt. % of polyoxyethylene sorbitan monopalmitate.

At the same time, the culture medium was passed through a flat membrane microfilter, which had been previously sterilized, in an amount of feeding rate of the feed solution +20 ml each/hr to fractionate into 20 ml of the cell-containing solution and the filtrate. The cell-containing solution was returned to the jar fermenter. From the cell-free filtrate, L-glutamic acid was collected by crystallization.

Figure 4A:
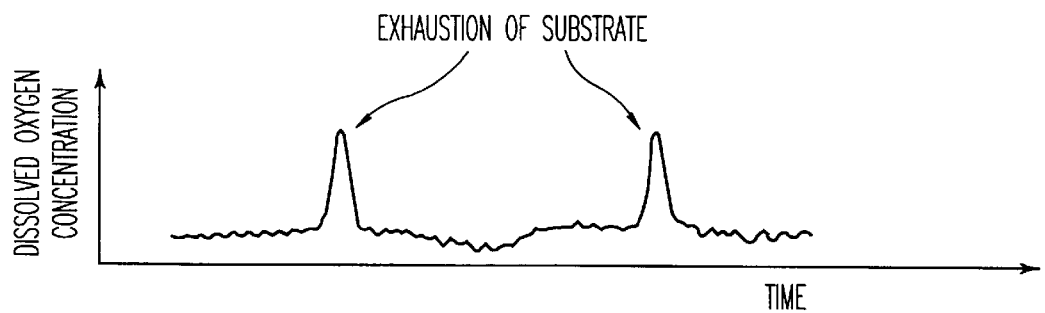
FIG. 4 represents the conditions for the feed culture in Example 1. The y axis represents the dissolved oxygen concentration in FIG. 4(a), pH 4(b) and sugar concentration in the fermenter in 4(c). The x axis represents increasing time in FIGS. 4(a)–(c).
Figure 4B:
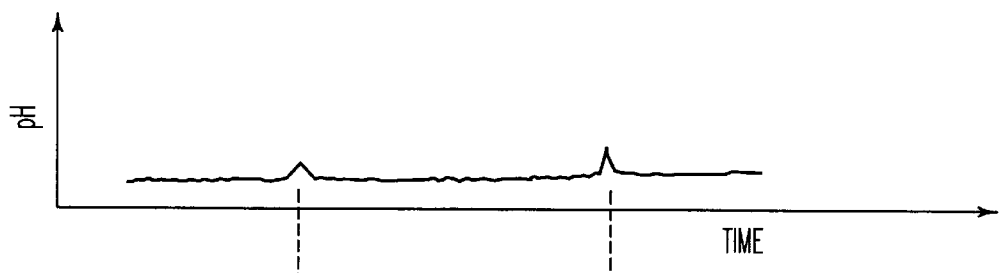
Figure 4C:
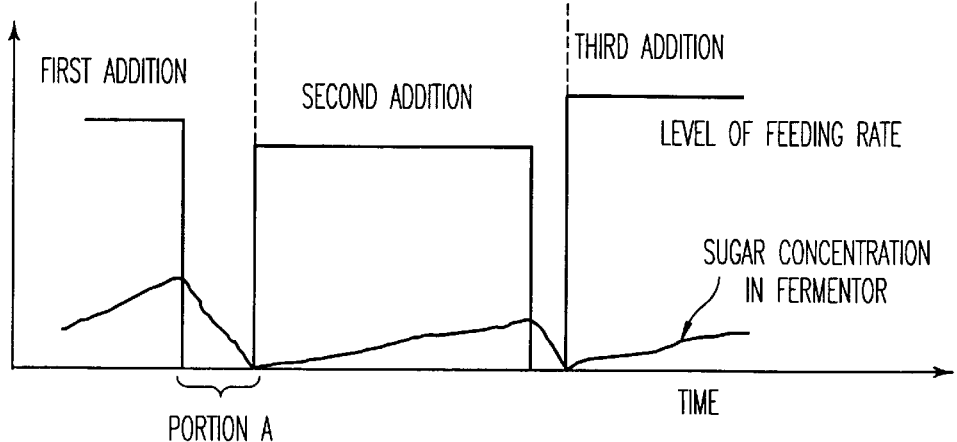

After the first addition of the feed solution was initiated, the computer began to automatically operate and at the point of time when the predetermined time (3 hours) for adding the feed solution lapsed, the addition of the feed solution was automatically terminated following the conditions set forth. As the addition was discontinued, the sugar concentration in the jar fermenter decreased as shown by portion A in FIG. 4 and became substantially 0 g/l. At this point of time, both the pH and the dissolved oxygen concentration increased almost at the same time.

At the point of time when either the pH or the dissolved oxygen concentration reached the early detection level of substrate exhaustion, the computer immediately computes and sets forth the feeding rate of the feed solution for the second addition. The determined level was transmitted to the feed pump. Again, the feed solution was added for 3 hours at the determined level of the rate. By repeating this procedure thereafter, the sugar concentration in the jar fermenter was controlled to 0 to 2 g/l with good accuracy.

The feeding rate of the feed solution in the additions following the second addition was set forth by the following rule, based on the time period ($\tau$) when the addition of the feed solution was terminated and the feeding rate (v) immediately before the addition of the feed solution was terminated.

If $\tau \leq 10$ minutes, set forth the feeding rate of a fresh feed solution at 1.1 v. Herein, v designates the feeding rate in the period for the addition immediately before.

If 10 minutes $<\tau \leq 30$ minutes, set forth a new feeding rate at v.

If 30 minutes $<\tau \leq 1$ hour, set forth a new feeding rate at 0.9 v.

If 1 hour $<\tau \leq 2$ hours, set forth a new feeding rate at 0.8 v.

Herein, the coefficient of v and $\tau$ sometimes vary depending upon conditions for cultivation such as type of cultivation, kind of substrate, property of bacteria used, and the like. The number of rules may be appropriately decreased or increased. For information, in the cultivation of this Example, it was already confirmed by preliminary experiment that there was no chance to satisfy $\tau<2$ hours. Furthermore, the time period for adding the feed solution was set forth 3 hours every time in this Example; however, as described above, it is unnecessary to keep the addition time constant, so long as the time within such a range that the activity of bacteria does not change greatly.

Figure 5:
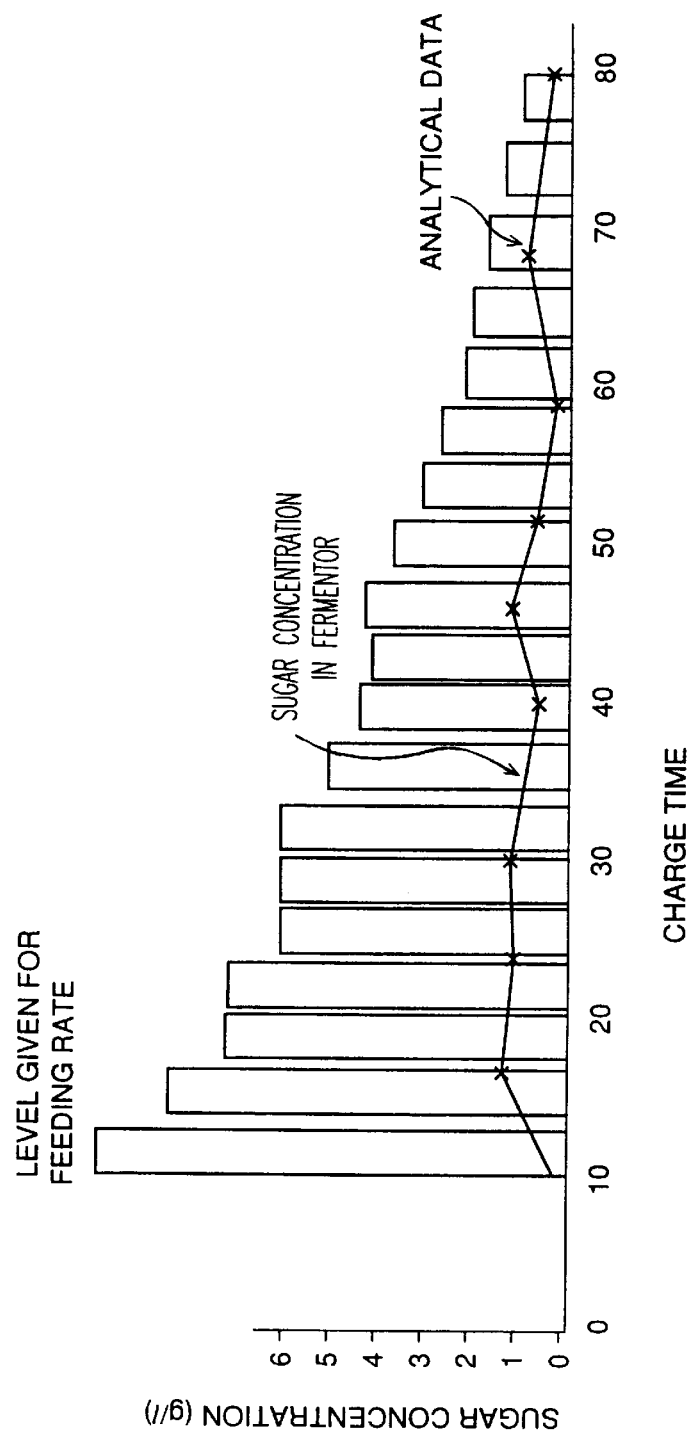
FIG. 5 shows the state of controlling the sugar concentration (y axis) over a period of time, hours (x axis) in Example 1.

By continuing the cultivation for 80 hours, 132 g of L-glutamic acid was obtained. After automatic running started, the sugar concentration could be stably controlled with 2 g/l completely automatically, as shown in FIG. 5.

Comparative Example 1

(Prior Art)

The prior art is characterized by using $NH_3$ for controlling pH and feeding sugar (feed solution) in proportion to the amount of used $NH_3$.

The seed culture medium obtained in a manner similar to Example 1 and 270 ml of the same main culture medium as in Example 1 were charged in a small-sized glass-made jar fermenter having a 1 liter volume, which had been previously sterilized. The mixture was kept at 30° C. and filter-sterilized air was bubbled at a rate of 300 ml/min. Stirring was initiated, while keeping the pH at 7.5 with $NH_3$ gas (initiation of the main cultivation).

The small-sized glass-made jar fermenter was connected with a 16 bit personal computer as shown in FIG. 3.

Five hours after the initiation of the main cultivation, polyoxyethylene sorbitan monopalmitate was added in a concentration of 0.2%. And after the main cultivation was continued for further 5 hours, the personal computer was put under the controllable state.

The analog signals were taken up in the personal computer from a mass flow meter connected with $NH_3$ gas line via the A/D converter built in the personal computer. After the feeding rate for the feed solution in an amount proportional to the amount of $NH_3$ added was computed every hour, the computer was programmed to send the feeding rate as analog signals to the feed pump via the D/A converter built in the personal computer.

Figure 6:
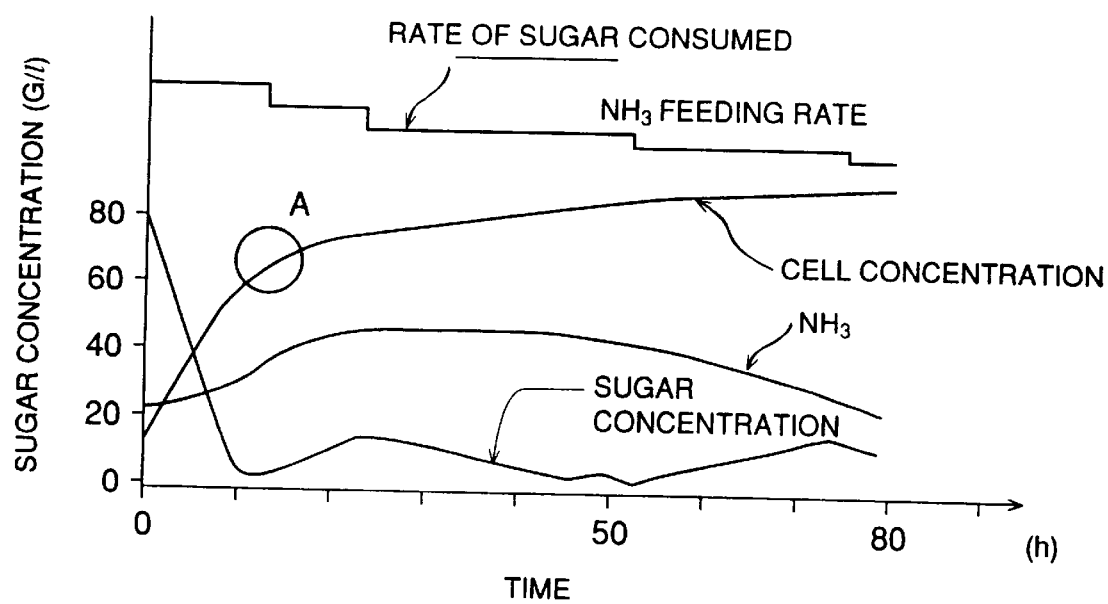
FIG. 6 shows the conditions for cultivation in Comparative Example 1. The y axis represents the sugar concentration, the x axis represents time (hours).

FIG. 6A illustrates the results by showing the ratio of the feeding rate of $NH_3$ to the feeding rate of the feed solution during the cultivation that entered from the cell growth phase into the phase of producing L-glutamic acid, wherein the control of the sugar cultivation became poor. Thus, the proportional coefficient was changed 13 hours after. Even after the change, this proportional coefficient was unstable so that the control of the sugar concentration in the jar fermenter was not good as compared to FIG. 5. Therefore, the concentration of the remaining sugar (sugar concentration in the jar fermenter) was monitored 5 times. Because of such instability, it was impossible to reduce the concentration of the remaining sugar to a very low level during the cultivation, so as to avoid the sugar concentration being 0 g/l.

By continuing the cultivation for 80 hours, 120 g of L-glutamic acid was produced but this amount was lower than 132 g in the production amount in Example 1.

The results of Example 1 and Comparative Example 1 are summarized in Table 1.

TABLE 1

| Item for Comparison | Comparative Example 1 (Prior Art) | Example 1 (Invention) |
|---|---|---|
| Controllable concentration of sugar in cultivation (g/l) | 5–20 | 0–2 |
| Time for feed culture (h) | 80 | 80 |
| Number of times of monitoring the concentration of remaining sugar | 5 | 0 |
| Timer for manual adjustment of the ratio of rate of sugar consumed to the feeding rate of $NH_3$ | 5 | 0 |
| Amount of sugar flown out of the system (g) | 28.5 | 0.1 |
| Amount of glutamic acid produced (g) | 120 | 132 |

Example 2
Production of L-phenylalanine by fermentation in fed-batch culture

L-Phenylalanine was produced by fermentation using *Brevibacterium lactofermentum* FERM BP-1071 in a manner similar to Example 1, except for changing the cell-recycling continuous culture to fed-batch culture.

The medium, cultivation vessel, the method for time course for the cultivation, and method for controlling the feeding rate of the feed solution were also modified as follows.

(1) Medium (a) Medium for Seed Culture

| | |
|---|---|
| Sucrose | 2.0 g/dl |
| Phosphoric acid | 0.1 g/dl |
| $MgSO_4$ | 40 mg/dl |
| $FeSO_4$ | 1 mg/dl |
| $MnSO_4$ | 1 mg/dl |
| Urea | 0.3 g/dl |
| Ammonium acetate | 0.2 g/dl |
| Tyrosine | 50 mg/dl |
| KOH | 70 mg/dl |
| Protein hydrolysate (as total nitrogen) | 200 mg/dl |
| Biotin | 100 µg/l |
| Vitamin $B_1$ | 100 µg/l |
| Silicone defoaming agent | 20 µg/l |
| pH | 7.5 |
| sterilized | 120° C., 20 minutes |

(b) Medium for Seed Culture

| | |
|---|---|
| Glucose | 15 g/dl |
| $MgSO_4$ | 28 mg/dl |
| $MnSO_4$ | 1 mg/dl |
| Phosphoric acid | 90 mg/dl |
| Biotin | 50 µg/dl |
| Vitamin $B_1$ | 2 µg/dl |
| Protein hydrolysate (as total nitrogen) | 870 mg/dl |
| Tyrosine | 100 mg/dl |
| KOH | 70 mg/dl |
| Silicone defoaming agent | 2 µg/l |
| pH | 7.5 |
| sterilized | 120° C., 20 minutes |

(c) Feed Medium

Same as in the main medium except that 25 g/dl of glucose was used.

(2) Cultivation vessel and method for cultivation (a) Seed culture: After 30 ml of medium for seed culture was charged in a flask of 500 ml volume, cultivation was carried out at 30° C. while shaking.

(b) Main culture: After 30 ml seed culture broth and 270 ml of medium for main culture were charged in a small-sized glass-made jar fermenter of 1 liter volume, aerobic cultivation was carried out at 30° C. (amount of air was 150 ml/min.). The pH was adjusted to 7.5 with $NH_3$.

(3) Time for cultivation (a) seed culture: 48 hours (b) main culture: 96 hours (c) time for starting the feeding: 35 hours after the main culture started.

(4) Method for controlling the feeding rate of feed solution

The feeding rate was controlled in a manner similar to Example 1, except that the initial feeding rate was set forth at 10 ml/h.

Comparative Example 2
Prior Art

Using $NH_3$, the pH was adjusted and the feeding rate of feed solution was controlled using the pH as an index. That is, when the pH was increased more than the level set forth, the feeding rate was increased by 5% and where the increase in pH was not noted for 5 hours, the feeding rate was decreased by 10%.

The results of Example 2 and Comparative Example 2 are summarized in Table 2.

TABLE 2

| Item for Comparison | Comparative Example 2 | Example 2 |
|---|---|---|
| Controllable concentration of sugar in feed culture (g/l) | 10–30 | 0–3 |
| Time for cultivation (h) | 96 | 96 |
| Amount of sugar flown out of the system (g) | 10.5 | <0.2 |
| Amount of phenylalanine produced (g) | 13 | 15.5 |

Example 3
Production of yeast cell by fed-batch culture

Yeast cell was produced by fermentation using *Saccharomyces cerevisiae* CBS 1523 in a manner similar to Example 1, except for changing the cell-recycling continuous culture to fed-batch culture.

The medium, cultivation vessel, method for cultivation and method for controlling the feeding rate of the feed solution were also modified as follows.

(a) Medium for Seed Culture

| | |
|---|---|
| Glucose | 3 g/dl |
| KH$_2$PO$_4$ | 0.1 g/dl |
| Ammonium sulfate | 0.5 g/dl |
| MgSO$_4$ | 0.05 g/dl |
| Protein hydrolysate (as total nitrogen) | 0.1 g/dl |
| Yeast extract | 0.1 g/dl |
| pH | 6.5 |
| sterilized | 120° C., 15 minutes |

(b) Medium for Main Culture

| | |
|---|---|
| Glucose | 5 g/dl |
| KH$_2$PO$_4$ | 0.1 g/dl |
| Ammonium sulfate | 1.0 g/dl |
| MgSO$_4$ | 0.05 g/dl |
| Corn steep liquor | 0.2 g/dl |
| pH | 6.5 |
| sterilized | 120° C., 15 minutes |

(c) Feed Medium

Same as in the main medium except that 50 g/dl of glucose was used and 5 g/dl of ammonium sulfate was used.

(2) Cultivation vessel and method for cultivation (a) Seed culture: After 30 ml of medium for seed culture was charged in a flask of 500 ml volume, cultivation was carried out at 30° C. for 24 hours while shaking.

(b) Main culture: After 30 ml of seed culture broth and 270 ml of the medium for main culture were charged in a small-sized glass-made jar fermenter of 1 liter volume, aerobic cultivation was carried out at 30° C. for 10 hours (amount of air was 150 ml/ml). The pH was adjusted to 6.5 with NH$_3$. Furthermore, the feed solution (medium) began to add 10 hours after the main culture started.

(3) Method for controlling the feeding rate of feed solution

The feeding rate was controlled in a manner similar to Example 1, except that the initial feeding rate was set forth at 5 ml/hr.

Comparative Example 3
(Prior Art)

The feeding rate of the feed solution was controlled, using as an index, the rate of forming ethanol by-product (ethanol gas in exhaust gas was measured). That is, when the rate of ethanol formation was increased more than the level set forth, the feeding rate was decreased and where the rate was decreased below the level set forth, the feeding rate was increased.

The results of Example 3 and Comparative Example 3 are summarized in Table 3.

| Item for Comparison | Comparative Example 3 | Example 3 |
|---|---|---|
| Controllable concentration of sugar in feed culture (g/l) | 5–20 | 0–3 |
| Time for cultivation (h) | 50 | 50 |
| Amount of ethanol formed (g) | 5–10 | 0–5 |
| Dry weight of yeast cell (g) | 39 | 48 |

Example 4

Production of L-Threonine by fermentation in fed-batch culture

L-Threonine was produced by fermentation using *Brevibacterium flavum* FERM BP-1173 in a manner similar to Example 1, except for changing the cell-recycling continuous culture to fed-batch culture.

The medium, cultivation vessel, the method for cultivation, time course for the cultivation, and method for controlling the feeding rate of the feed solution were modified as follows.

(1) Medium

(a) Medium for Seed Culture

| | |
|---|---|
| Glucose | 2.0 g/dl |
| KH$_2$PO$_4$ | 0.1 g/dl |
| MgSO$_4$ | 40 mg/dl |
| FeSO$_4$ | 1 mg/dl |
| MnSO$_4$ | 1 mg/dl |
| Urea | 0.3 g/dl |
| Ammonium acetate | 0.2 g/dl |
| Protein hydrolysate (as total nitrogen) | 200 g/dl |
| Biotin | 100 µg/l |
| Vitamin B$_1$ | 100 µg/l |
| Silicone defoaming agent | 20 µg/l |
| pH | 7.5 |
| sterilized | 120° C., 20 minutes |

(b) Medium for Main Culture

| | |
|---|---|
| Glucose | 5 g/dl |
| MgSO$_4$ | 40 mg/dl |
| MnSO$_4$ | 1 mg/dl |
| Phosphoric acid | 200 mg/dl |
| Biotin | 50 µg/l |
| Vitamin B$_1$ | 5 mg/l |
| Protein hydrolysate (as total nitrogen) | 100 mg/dl |
| KOH | 150 mg/dl |
| Silicone defoaming agent | 2 µg/l |
| pH | 7.5 |
| sterilized | 120° C., 20 minutes |

(c) Feed Medium 50 g/dl aqueous solution of acetic acid was used.

(2) Cultivation vessel and method for cultivation (a) Seed culture: After 30 ml of medium for seed culture was charged in a flask of 500 ml volume, cultivation was carried out at 30° C. while shaking.

(b) Main culture: After 30 ml of seed culture broth and 270 ml of medium for main culture were charged in a small-sized glass-made jar fermenter of 1 liter volume, aerobic cultivation was carried out at 30° C. (amount of air was 150 ml/min.). The pH was adjusted to 7.5 with NH$_3$.

(3) Time for cultivation (a) seed culture: 40 hours (b) main culture: 100 hours (c) time for starting the feeding: 20 hours after the main culture started.

(4) Method for controlling the feeding rate of feed solution

The feeding rate was controlled in a manner similar to Example 1, except that the initial feeding rate was set forth at 1.5 ml/h.

Comparative Example 4
(Prior Art)

The feeding rate of feed solution was controlled using the pH as an index. That is, when the pH was increased more than the level set forth, the feed solution was added at constant time by the feeding rate of 0.5 ml/min using an on-off timer.

The results of Example 4 and Comparative Example 4 are summarized in Table 4.

| Item for Comparison | Comparative Example 2 | Example 2 |
|---|---|---|
| Controllable concentration of acetic acid in feed culture (g/l) | 10–30 | 0–3 |
| Time for cultivation (h) | 100 | 100 |
| Amount of acetic acid flown out of the system (g) | 5.2 | <0.2 |
| Amount of produced (g) | 7.8 | 8.8 |

Example 5
Production of Guanosine by fermentation in fed-batch culture

Guanosine was produced by fermentation using *Bacillus subtilis* FERM BP-3601 in a manner similar to Example 1, except for changing the cell-recycling continuous culture to fed-batch culture.

The medium, cultivation vessel, method for cultivation, time course for the cultivation and method for controlling the feeding rate of the feed solution were modified as follows:

(1) Medium (a) Medium for Seed Culture

| | |
|---|---|
| Glucose | 3.0 g/dl |
| Phosphoric acid | 0.04 g/dl |
| $MgSO_4$ | 40. mg/dl |
| $FeSO_4$ | 1 mg/dl |
| $MnSO_4$ | 1 mg/dl |
| RNA | 0.5 g/dl |
| Ammonium chloride | 0.3 g/dl |
| Yeast extract | 50 mg/dl |
| KOH | 70 mg/dl |
| Protein hydrolysate (as total nitrogen) | 200 mg/dl |
| Silicone defoaming agent | 20 mg/dl |
| pH | 6.5 |
| sterilized | 120° C., 20 minutes |

(b) Medium for Main Culture

| | |
|---|---|
| Glucose | 20 g/dl |
| $MgSO_4$ | 15 mg/dl |
| $MnSO_4$ | 1 mg/dl |
| Phosphoric acid | 90 mg/dl |
| Ammonium chloride | 0.5 g/dl |
| Karium chloride | 1.5 g/dl |
| Protein hydrolysate (as total nitrogen) | 150 mg/dl |
| RNA | 0.125 g/dl |
| DL-Methionine | 50 mg/dl |
| KOH | 60 mg/dl |
| Silicone defoaming agent | 2 μg/l |
| pH | .5 |
| sterilized | 120° C., 20 minutes |

(c) Feed Medium 0.50 g/dl aqueous solution of glucose was used.

(2) Cultivation vessel and method for cultivation (a) Seed culture: After 30 ml of medium for seed culture was charged in a flask of 500 ml volume, cultivation was carried out at 30° C. while shaking.

(b) Main culture: After 30 ml of seed culture broth and 270 ml of medium for main culture were charged in a small-sized glass-made jar fermenter of 1 liter volume, aerobic cultivation was carried out at 30° C. (amount of air was 200 ml/min.). The pH was adjusted to 6.5 with $NH_3$.

(3) Time for cultivation (a) seed culture: 30 hours (b) main culture: 150 hours (c) time for starting the feeding: 50 hours after the main culture started (4) Method for controlling the feeding rate of feed solution The feeding rate was controlled in a manner similar to Example 1, except that the initial feeding rate was set forth at 1 ml/h.

Comparative Example 5
(Prior Art)

Using $NH_3$, the pH was adjusted and the feeding rate of feed solution was controlled using the pH as an index. That is when the pH was increased more than the level set forth, the feeding rate was increased by 5% and where the increase in pH was not noted for 5 hours, the feeding reate was decreased by 10%.

The results of Example 5 and Comparative Example 5 are summarized in Table 5.

TABLE 5

| Item for Comparison | Comparative Example 2 | Example 2 |
|---|---|---|
| Controllable concentration of sugar in feed culture (g/l) | 10–30 | 0–3 |
| Time for cultivation (h) | 150 | 150 |
| Amount of sugar flown out of the system (g) | 15.0 | <0.2 |
| Amount of Guanosine produced (g) | 10.4 | 13.0 |

Example 6

A medium containing 30 g/l of glucose, 10 g/l of ammonium chloride, 3 g/l or urea, 1 g/l of $KH_2PO_4$, 100 mg/l of $MgSO_4.7H_2O$, 10 mg/l of $FeSO_4.7H_2O$, 8 mg/l of $MnSO_4.4H_2O$, 1 g/l (when calculated as nitrogen) of soybean protein acid hydrolysate, 0.1 mg/l of thiamine hydrochloride and 0.3 mg/l of biotin was separately charged by 20 ml each in 3 shake flasks having a volume of 500 ml each. After the medium was sterilized by heating at 115° C. for 10 minutes, one platinum loop of *Brevibacterium lactofermentum* ATCC 21800, which had been previously grown on bouillon slant for 48 hours, was inoculated on the medium followed by shake culture at 31.5° C. for 24 hours. The foregoing procedures were for seed culture.

Medium (pH 7.0) containing 80 g/l of molasses (calculated as sugar), 50 g/l of ammonium sulfate, 1 g/l of $KH_2PO_4$, 1 g/l of $MgSO_4.7H_2O$, 100 mg/l (when calculated as nitrogen) of soybean protein acid hydrolysate, 0.1 mg/l of thiamine hydrochloride and 0.3 mg/l of biotin was separately charged by 300 ml each in 3 small-sized fermenters having a volume of 1 liter. The medium was sterilized by heating at 120° C. for 15 minutes. After cooling to 31.5° C., the aforesaid medium which completed incubation in the flask was added to the fermenters in an amount of 15 ml each/fermenter. Incubation was performed under conditions of temperature of 31.5° C., an air flow rate of ½ vvm and the stirring number of 700 rpm.

With one out of the 3 fermenters, the incubation was terminated at the time when the sugar in the medium was used up (conventional batch incubation) and the concentration of L-lysine accumulated in the medium was quantitatively determined by acidic copper ninhydrin colorimetry. In the other two fermenters, the feed medium began to be fed at the time when the sugar concentration in the medium became 5 g/l or less. In one of the fermenter, the feed medium contained glucose (40 g/l) alone (conventional feed culture) and in the fermenter of the present invention, the feed medium contained glucose (40 g/l), soybean protein hydrolysate (100 mg/l as nitrogen), thiamine hydrochloride (0.1 mg/l) and biotin (0.3 mg/l). While controlling the feeding velocity of the feed medium so as to keep the sugar concentration in the culture broth on the level of 5 g/l or less, incubation was carried out in these fermenters. After 100 ml of the feed medium was fed to each culture, incubation was completed at the time when the sugar in the culture broth was used up. The concentration of L-lysine accumulated in the culture broth was quantitatively determined.

The results of incubation in the 3 fermenters are shown in Table 6.

TABLE 6

| Method of Fermentation | L-Lysine Productivity (g/l · hr) | Yield of L-Lysine (%) |
| --- | --- | --- |
| Batch culture (prior art) | 2.2 | 32 |
| Feed culture (prior art) | 2.3 | 33 |
| This invention | 2.8 | 35 |

It is understood from Table 6 that the productivity and yield of L-lysine are both excellent.

Example 7

A medium containing 30 g/l of glucose, 10 g/l of ammonium chloride, 3 g/l of urea, 1 g/l of $KH_2PO_4$, 100 mg/l of $MgSO_4 \cdot 7H_2O$, 10 mg/l of $FeSo_4 \cdot 7H_2$), 8 mg/l of $MnSO_4 \cdot 4H_2O$, 100 mg/l (when calculated as nitrogen) of soybean protein acid hydrolysate, 0.1 mg/l of thiamine hydrochloride and 0.3 mg/l of biotin was separately charged by 20 ml each in 2 shake flasks having a volume of 500 ml each. After the medium was sterilized by heating at 115° C. for 10 minutes, one platinum loop of *Brevibacterium flavum* ATCC 21475, which had been previously grown on bouillon slant for 48 hours, was inoculated on the medium followed by shake culture at 31.5° C. for 24 hours. The foregoing procedures were for seed culture.

Medium (pH 7.0) containing 80 g/l of molasses (calculated as sugar), 50 g/l of ammonium sulfate, 1 g/l of $KH_2PO_4$, 1 g/l of $MgSO_4 \cdot 7H_2O$, 100 mg/l (when calculated as nitrogen) of soybean protein acid hydrolysate, 0.1 mg/l of thiamine hydrochloride and 0.3 mg/l of biotin was separately charged by 300 ml each in 2 small-sized fermenters having a volume of 1 liter. The medium was sterilized by heating at 120° C. for 15 minutes. After cooling to 31.5° C., the aforesaid medium which completes the incubation was added to the fermenters in an amount of 15 ml each/fermenter. Incubation was performed under conditions of temperature of 31.5° C., an air flow rate of ½ vvm and the stirring number of 700 rpm.

The feed medium began to be fed at the time when the sugar concentration in the culture broth became 5 g/l or less. The feed medium contained glucose (40 g/l), soybean protein hydrolysate (100 mg/l as nitrogen), thiamine hydrochloride (0.1 mg/l) and biotin (0.3 mg/l). In one fermenter, incubation was continued while controlling the feeding velocity of the feed medium so as to keep the sugar concentration in the culture broth constantly at the level of 5 g/l or less (present invention). In another fermenter, incubation was continued at such a feeding velocity that the sugar concentration became in the range of 5 to 15 g/l (comparison). After 100 ml of the feed medium was fed to each culture, incubation was completed at the time when the sugar in the culture broth was used up. The concentration of L-lysine accumulated in the culture broth was quantitatively determined.

The results of incubation in the 2 fermenters are shown in Table 7.

TABLE 7

| Control of Sugar Level (g/l) | L-Lysine Productivity (g/l · hr) | Yield of L-Lysine (%) |
| --- | --- | --- |
| Less than 5 (present invention) | 2.9 | 34 |
| 5–15 (comparison) | 2.5 | 32 |

Example 8

A medium containing 30 g/l of glucose, 10 g/l of ammonium chloride, 3 g/l or urea, 1 g/l of $KH_2PO_4$, 100 mg/l of $MgSO_4 \cdot 7H_2O$, 10 mg/l of $FeSO_4 \cdot 7H_2O$, 8 mg/l of $MnSO_4 \cdot 4H_2O$, 1 g/l (when calculated as nitrogen) of soybean protein acid hydrolysate, 0.1 mg/l of thiamine hydrochloride and 0.3 mg/l of biotin was separately charged by 20 ml each in 3 shake flasks having a volume of 500 ml each. After the medium was sterilized by heating at 115° C. for 10 minutes, one platinum loop of *Brevibacterium flavum* ATCC 21475, which had been previously grown on bouillon slant for 48 hours, was inoculated on the medium followed by shake culture at 31.5° C. for 24 hours. The foregoing procedures were for seed culture.

Medium (pH 7.0) containing 80 g/l of molasses (calculated as sugar), 50 g/l of ammonium sulfate, 1 g/l of $KH_2PO_4$, 1 g/l of $MgSO_4 \cdot 7H_2O$, 100 mg/l (when calculated as nitrogen) of soybean protein acid hydrolysate, 0.1 mg/l of thiamine hydrochloride and 0.3 mg/l of biotin was separately charged by 300 ml each in 3 small-sized fermenters having a volume of 1 liter. The medium was sterilized by heating at 120° C. for 15 minutes. After cooling to 31.5° C., the aforesaid medium (seed culture medium) which complete incubation in the flask was added to the fermenters in an amount of 15 ml. Incubation was performed under conditions of temperature of 31.5° C., an air flow rate of ½ vvm and the stirring number of 700 rpm.

The feed medium began to be fed at the time when the sugar concentration in the culture broth became 5 g/l or less. The feed medium of the present invention contained glucose (40 g/l), soybean protein hydrolysate (100 mg/l as nitrogen), thiamine hydrochloride (0.1 mg/l) and biotin (0.3 mg/l). While controlling the feeding velocity of the feed medium so as to keep the sugar concentration in the medium always on the level of 5 g/l or less, incubation was carried out. After 100 ml of the feed medium was fed to the culture, 100 ml of the medium was withdrawn from the fermenter at the time when the sugar in the culture broth was used up.

While further feeding the feed medium, incubation was continued. Also in this case, the sugar concentration in the culture broth was set forth to keep the level at 5 g/l or less. After 100 ml of the feed medium was fed, incubation was terminated at the time when the sugar in the culture broth was used up. The medium in the fermenter and the medium previously withdrawn were combined and the concentration of L-lysine accumulated therein was quantitatively determined.

The results reveal that the productivity of lysine was 3.8 g/l.hr and the yield of lysine was 42%.

Example 9

A medium containing 30 g/l of glucose, 10 g/l of ammonium chloride, 3 g/l of urea, 1 g/l of $KH_2PO_4$, 100 mg/l of $MgSO_4.7H_2O$, 10 mg/l of $FeSO_4.7H_2O$, 8 mg/l of $MnSO_4.4H_2O$, 1 g/l (when calculated as nitrogen) of soybean protein acid hydrolysate, 0.1 mg/l of thiamine hydrochloride and 0.3 mg/l of biotin was separately charged by 20 ml each in two shake flasks having a volume of 500 ml each. After the medium was sterilized by heating at 115° C. for 10 minutes, one platinum loop of *Corynebacterium acetoglutamicum* ATCC 21491, which had been previously grown on a bouillon slant for 48 hours, was inoculated on the medium followed by shake culturing at 31.5° C. for 24 hours. The foregoing procedures were for seed culture.

Medium (pH 7.0) containing 80 g/l of molasses (calculated as sugar), 50 g/l of ammonium sulfate, 1 g/l of $KH_2PO_4$, 1 g/l of $MgSO_4.7H_2O$, 100 mg/l (when calculated as nitrogen) of soybean protein acid hydrolysate, 0.1 mg/l of thiamine hydrochloride and 0.3 mg/l of biotin was separately charged by 300 ml each in 2 small-sized fermenters having a volume of 1 liter. The medium was sterilized by heating at 120° C. for 15 minutes. After cooling to 31.5° C., the aforesaid medium which complete incubation in the flask was added to the fermenters in an amount of 15 ml each/fermenter. Incubation was performed under conditions of temperature of 31.5° C., an air flow rate of ½ vvm and the stirring number of 700 rpm.

In one of the fermenters, the feed medium began to be fed at the time when the sugar concentration in the culture broth became 5 g/l or less. The feed medium contained glucose (40 g/l), soybean protein hydrolysate (100 mg/l as nitrogen), thiamine hydrochloride (0.1 mg/l) and biotin (0.3 mg/l) (present invention). While controlling the feeding velocity of the feed medium so as to keep the sugar concentration in the culture broth always at the level at 5 g/l or less, incubation was continued. After 100 ml of the feed medium was fed, 100 ml of the broth was withdrawn from the fermenter at the time when the sugar in the broth was used up.

While further feeding the feed medium, incubation was continued. Also in this case, the sugar concentration in the medium was set forth to keep the level at 5 g/l or less. After 100 ml of the feed medium was fed, incubation was terminated at the time when the sugar in the culture broth was used up. The culture broth in the fermenter and the broth previously withdrawn were combined and the concentration of L-lysine accumulated therein was quantitatively determined.

The results reveal that the productivity of lysine was 3.9 g/l.hr and the yield of lysine was 41%.

With respect to the other fermenter, feed medium for continuous culture began to be fed 25 hours after incubation started. As the feed medium, a medium obtained by diluting the initial medium to 4-fold was used. About 1 liter of the feed medium was flown in a dilution magnification of 0.05 $hr^{-1}$ to perform continuous culture. After the constant state was reached, the concentration of L-lysine in the medium was quantitatively determined.

The results reveal that the productivity of lysine was 3.5 g/l.hr and the yield of lysine was 35%.

According to the present invention as shown in Examples 6 through 9, L-lysine can be produced by fermentation with high productivity as in convention continuous process, while maintaining the high concentration of the product accumulated and the high yield as achieved by fermentation in the conventional batch process. Thus, the productivity can be greatly improved and the costs can be reduced in the industrial production of L-lysine by using the present invention.

While the foregoing invention has been described in some detail for purposes of clarity and understanding it will be appreciated by one skilled in the art from the reading of this disclosure that various changes in form and detail can be made without departing from the true scope of the invention.

We claim:

1. A method for aerobically cultivating yeast or bacteria in a culture medium of fed-batch, continuous or cell-recycling continuous cultures, comprising maintaining a carbon source concentration in said culture medium at a constant low level of under 5 g/l, wherein said carbon source concentration is maintained by:

(1) determining a volume of the carbon source to be used in a first feeding (So) by:
   (a) measuring in a preliminary culture of said yeast or bacteria an average carbon consumption rate (v), wherein said average carbon consumption rate is determined at a time after the culture is started when the carbon source in the culture is exhausted;
   (b) measuring a feeding time (T) wherein activity of the yeast or bacteria in the preliminary culture in the presence of the carbon source does not change; and
   (c) setting a volume of the carbon source to be used in a first feeding (So) of a main culture as So=v×T;

(2) starting the main culture of the yeast or bacteria;

(3) adding to said main culture the first feeding of a volume of the carbon source (So) for the time (T);

(4) detecting exhaustion of the carbon source as an increase in pH or an increase in concentration of oxygen dissolved in the culture medium;

(5) adding to said main culture at least a second feeding of the volume of the carbon source for the time (T), wherein a feeding rate is determined based on a period (τ) before which the second feeding is added as follows:
   if 10 min.≧τ, the feeding rate of the feed solution is set at 1.1×v;
   if 30 min.≧τ>10 min., the feeding rate of the feed solution is set at v;
   if 60 min.≧τ>30 min., the feeding rate of the feed solution is set at 0.9×v; or
   if 120 min.≧τ>60 min., the feeding rate of the feed solution is set at 0.8×v.

2. The method of claim 1, wherein said carbon source is sugar.

3. The method of claim 1, wherein said carbon source concentration in said cultivation vessel at a level of under 3 g/l.

* * * * *